United States Patent [19]
Wakimasu et al.

[11] Patent Number: 5,948,754
[45] Date of Patent: Sep. 7, 1999

[54] CYCLIC HEXAPEPTIDES, THEIR PRODUCTION AND USE

[75] Inventors: Mitsuhiro Wakimasu; Takashi Kikuchi, both of Osaka; Akira Kawada, Ibaraki, all of Japan

[73] Assignee: Takeda Chemical Industries, Ltd., Osaka, Japan

[21] Appl. No.: 08/739,810

[22] Filed: Oct. 30, 1996

Related U.S. Application Data

[63] Continuation of application No. 08/332,515, Oct. 31, 1994, abandoned.

[30] Foreign Application Priority Data

Nov. 8, 1993 [JP] Japan ................................. 5-278722
May 26, 1994 [JP] Japan ................................. 6-112365

[51] Int. Cl.$^6$ .............................. A61K 38/12; C07K 7/64
[52] U.S. Cl. .................................. 514/11; 514/9; 514/2; 530/317; 530/339
[58] Field of Search ..................... 514/11, 9, 2; 530/317, 530/339

[56] References Cited

U.S. PATENT DOCUMENTS 5,114,918  5/1992  Ishikawa et al. ........................ 514/11

FOREIGN PATENT DOCUMENTS 0 528 312  2/1993  European Pat. Off. .
0 552 417  7/1993  European Pat. Off. .
0 555 537  8/1993  European Pat. Off. .

OTHER PUBLICATIONS

Kikuchi et al. "Cyclic Hexapeptide Endothelin Receptor Antagonists Highly Potent For Both Receptor Subtypes ET$_A$ and ET$_B$", *Biochemical and Biophysical Research Communications*, vol. 200:1708–1711, (1994).

Hirata et al. "Receptor Binding Activity and Cytosolic Free Calcium Response by Synthetic Endothelin Analogs in Cultured Rat Vascular Smooth Muscle Cells", Biochem. Biophysical Research Comm., vol. 160, No. 1, Apr. 1989, pp. 228–234.

Ihara et al., "Biological Profiles of Highly Potent Novel Endothelin Antagonists Selective for the ET$_A$ Receptor", Life Sciences, vol. 50, No. 4, (1992), pp. pp. 247–255.

Nakajima et al., "Structure–Activity Relationship of Endothelin: Importance of Charged Groups", Biochem. Biophysical Res. Comm., vol. 163, No. 1, (1989), pp. 424–429.

Kimura et al., "Structure–Activity Relationship of Endothelin: Importance of the C–Terminal Moiety", Biochem. Biophysical Res. Comm., vol. 156, No. 3, Nov. 1988, pp. 1182–1186.

Annette M. Doherty, "Endothelin: A New Challenge", Jour. of Med. Chem., vol. 35, No. 9, May 1992 pp. 1494–1508.

*Primary Examiner*—Ponnathapura Achutamurthy
*Assistant Examiner*—T. D. Wessendorf
*Attorney, Agent, or Firm*—Foley & Lardner

[57] ABSTRACT

A cyclic hexapeptide represented by the formula:

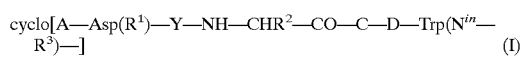

wherein A is a D-acidic-α-amino acid residue; Y is an acidic-α-amino acid residue; C is an L-α-amino acid residue; $R^1$ is a group represented by the formula:

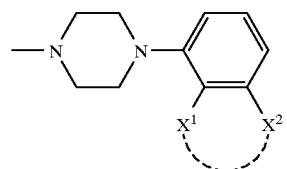

wherein $X^1$ and $X^2$ are independently H, $C_{1-6}$ alkyl, $C_{1-6}$ alkoxy, halogen or nitro, and may bind together to form a ring in cooperation with the adjacent carbon atom; $R^2$ is $C_{1-6}$ alkyl, $C_{3-7}$ cycloalkyl, $C_{3-7}$ cycloalkyl-$C_{1-3}$ alkyl, $C_{1-6}$ alkylthio-$C_{1-3}$ alkyl, $C_{3-7}$ cycloalkylthio-$C_{1-3}$ alkyl, $C_{1-5}$ alkoxy-$C_{1-3}$ alkyl, $C_{3-7}$ cycloalkoxy-$C_{1-3}$ alkyl, $C_{1-6}$ alkylthio, $C_{3-7}$ cycloalkylthio, $C_{1-5}$ alkoxy or $C_{3-7}$ cycloalkoxy; $R^3$ is H, $C_{1-6}$ alkyl, $C_{3-7}$ cycloalkyl, —COR$^4$, —COOR$^5$ or —CONHR$^6$; when $X^1$, $X^2$ and $R^3$ are all hydrogen atoms, $R^2$ is not an isobutyl group, or a salt thereof, which exhibits excellent antagonistic action against endothelin receptors, particularly endothelin B receptors.

5 Claims, No Drawings

CYCLIC HEXAPEPTIDES, THEIR PRODUCTION AND USE

This application is a continuation of application Ser. No. 08/332,515, filed Oct. 31, 1994, now abandoned.

BACKGROUND OF THE INVENTION

The present invention provides a cyclic hexapeptide or a salt thereof, a method of its production, and an endothelin receptor antagonist containing said cyclic hexapeptide or a pharmacologically acceptable salt thereof.

Endothelin (ET), a vasoconstrictive peptide comprising 21 amino acids, is isolated from the culture supernatant of the endothelial cells of porcine aortas and structurally determined by Yanagisawa et al. in 1988 [Yanagisawa et al., Nature, Vol. 332, pp. 411–412]. Research into endothelin-encoding genes has demonstrated that endothelin occurs in 3 structurally similar peptides, designated endothelin-1 (ET-1), endothelin-2 (ET-2) and endothelin-3 (ET-3), respectively.

On the other hand, two types of endothelin receptors are known: endothelin A receptors, which show higher affinity for ET-1 and ET-2 than for ET-3, and endothelin B receptors, which show equivalent affinity for ET-1, ET-2 and ET-3. In the part, endothelin A receptors were thought to be present in vascular smooth muscle and to induce smooth muscle contractions, endothelin B receptors to be present in vascular endothelial cells and to induce smooth muscle relaxation. In recent years, however, endothelin B receptors have been shown to be involved in vascular smooth muscle contractions as well [Biochemical and Biophysical Research Communications, Vol. 175(2), 556–561 (1991); Journal of Cardiovascular Pharmacology, Vol. 20 (Suppl. 12), S11–S14 (1992)]. There is therefore a need for the development of endothelin B receptor antagonists, as well as endothelin A receptor antagonists.

Since the development of endothelin, there have been intensive investigations in search of compounds that antagonize endothelin receptors, with the aim of developing therapeutic agents for diseases caused by endothelin. For example, cyclic peptides showing endothelin receptor antagonistic action are disclosed in EP0436189A1 and EP0528312A2. The cyclic peptide of Japanese Patent Unexamined Publication No. 261198/1992, in particular, is known to be very low in affinity for endothelin B receptors, though it has affinity for endothelin A receptors. The compound disclosed in Japanese Patent Unexamined Publication No. 261198/1992 is therefore faulty in that vascular smooth muscle contractions mediated by endothelin B receptors are not suppressed satisfactorily, though it suppresses vascular smooth muscle contractions mediated by endothelin A receptors.. On the other hand, the compound disclosed in EP0528312A2 is known to be an excellent endothelin receptor antagonist in that it has affinity not only for endothelin A receptors but also for endothelin B receptors. However, there is a need for development of an endothelin B receptor antagonist that shows better affinity for endothelin B receptors, so as to efficiently suppress vascular smooth muscle contractions mediated by such receptors.

The object of the present invention is to provide a compound having the antagonistic activity on endothelin B receptors with greater potency than for other types of endothelin receptors.

SUMMARY OF THE INVENTION

To solve the above problems, the present inventors investigated in search of a compound having the antagonistic activity on endothelin B receptors with greater potency than for other types of endothelin receptors, and found that a cyclic hexapeptide represented by the formula:

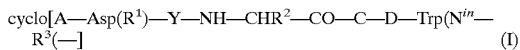

cyclo[A—Asp($R^1$)—Y—NH—CHR$^2$—CO—C—D—Trp($N^{in}$—R$^3$(—]  (I)

wherein A represents a D-acidic-α-amino acid residue; Y represents an acidic-α-amino acid residue; C represents an L-α-amino acid residue; $R^1$ represents a group represented by the formula:

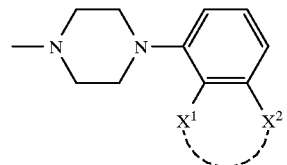

wherein $X^1$ and $X^2$ independently represent a hydrogen atom, a $C_{1-6}$ alkyl group, a $C_{1-6}$ alkoxy group, a halogen atom or a nitro group, and may bind together to form a ring in cooperation with the adjacent carbon atom; $R^2$ represents a $C_{1-6}$ alkyl group, a $C_{3-7}$ cycloalkyl group, a $C_{3-7}$ cycloalkyl-$C_{1-3}$ alkyl group, a $C_{1-6}$ alkylthio-$C_{1-3}$ alkyl group, a $C_{3-7}$ cycloalkylthio-$C_{1-3}$ alkyl group, a $C_{1-6}$ alkoxy-$C_{1-3}$ alkyl group, a $C_{3-7}$ cycloalkoxy-$C_{1-3}$ alkyl group, a $C_{1-6}$ alkylthio group, a $C_{3-7}$ cycloalkylthio group, a $C_{1-6}$ alkoxy group or a $C_{3-7}$ cycloalkoxy group; $R^3$ represents a hydrogen atom, a $C_{1-6}$ alkyl group, a $C_{3-7}$ cycloalkyl group, —COR$^4$ ($R^4$ represents a hydrogen atom, a $C_{1-6}$ alkyl group, a $C_{6-15}$ aryl group or a $C_{6-15}$ aryl-$C_{1-3}$ alkyl group), —COOR$^5$ ($R^5$ represents a $C_{1-6}$ alkyl group, a $C_{6-15}$ aryl group or a $C_{6-15}$ aryl-$C_{1-3}$ alkyl group) or —CONHR$^6$ ($R^6$ represents a hydrogen atom, a $C_{1-6}$ alkyl group, a $C_{6-15}$ aryl group or a $C_{6-15}$ aryl-$C_{1-3}$ alkyl group); when $X^1$, $X^2$ and $R^3$ are all hydrogen atoms, $R^2$ is not an isobutyl group, or a salt thereof, which the cyclic hexapeptide or a salt thereof is included in the scope of Claims of EP0528312A2 but not specifically produced in the Examples given in the specification therefore, exhibits more potent endothelin B receptor antagonistic action than against the cyclic hexapeptides or salts thereof specifically produced in Examples. The inventors made further investigations based on this finding, and developed the present invention.

Accordingly, the present invention relates to a cyclic hexapeptide represented by the formula:

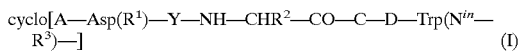

cyclo[A—Asp($R^1$)—Y—NH—CHR$^2$—CO—C—D—Trp($N^{in}$—R$^3$)—]  (I)

wherein A represents a D-acidic-α-amino acid residue; Y represents an acidic-α-amino acid residue; C represents an L-α-amino acid residue; $R^1$ represents a group represented by the formula:

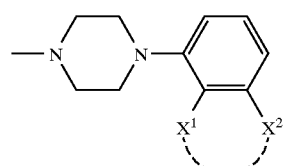

wherein $X^1$ and $X^2$ independently represent a hydrogen atom, a $C_{1-6}$ alkyl group, a $C_{1-6}$ alkoxy group, a halogen atom or a nitro group, and may bind together to form a ring in cooperation with the adjacent carbon atom; $R^2$ represents a $C_{1-6}$ alkyl group, a $C_{3-7}$ cycloalkyl group, a $C_{3-7}$ cycloalkyl-$C_{1-3}$ alkyl group, a $C_{1-6}$ alkylthio-$C_{1-3}$ alkyl group, a $C_{3-7}$ cycloalkylthio-$C_{1-3}$ alkyl group, a $C_{1-6}$ alkoxy-$C_{1-3}$ alkyl group, a $C_{3-7}$ cycloalkoxy-$C_{1-3}$ alkyl group, a $C_{1-6}$ alkylthio group, a $C_{3-7}$ cycloalkylthio group, a $C_{1-6}$ alkoxy group or a $C_{3-7}$ cycloalkoxy group; $R^3$ represents a hydrogen atom, a $C_{1-6}$ alkyl group, a $C_{3-7}$ cycloalkyl group, —$COR^4$ ($R^4$ represents a hydrogen atom, a $C_{1-6}$ alkyl group, a $C_{6-15}$ aryl group or a $C_{6-15}$ aryl-$C_{1-3}$ alkyl group), —$COOR^5$ ($R^5$ represents a $C_{1-6}$ alkyl group, a $C_{6-15}$ aryl group or a $C_{6-15}$ aryl-$C_{1-3}$ alkyl group) or —$CONHR^6$ ($R^6$ represents a hydrogen atom, a $C_{1-6}$ alkyl group, a $C_{6-15}$ aryl group or a $C_{6-15}$ aryl-$C_{1-3}$ alkyl group); when $X^1$, $X^2$ and $R^3$ are all hydrogen atoms, $R^2$ is not an isobutyl group, or a salt thereof, a method of production thereof, and an endothelin receptor antagonist, preferably an endothelin B receptor antagonist, that contains said cyclic hexapeptide of formula (I) or a pharmacologically acceptable salt thereof.

DESCRIPTION OF THE PREFERRED EMBODIMENTS

With respect to formula (I) above, A represents a D-acidic-α-amino acid residue. The D-acidic-α-amino acid residue is exemplified by D-amino acid residues having an acidic group, such as a carboxyl group, a sulfonyl group or a tetrazolyl group, in the side chain thereof. Such D-amino acid residues include D-glutamic acid, D-aspartic acid, D-cysteic acid, D-homocysteic acid, D-β-(5-tetrazolyl) alanine and D-2-amino-4-(5-tetrazolyl)butyric acid. D-glutamic acid, D-aspartic acid and D-cysteic acid are preferred, with greater preference given to D-aspartic acid.

With respect to formula (I) above, Y represents an acidic-α-amino acid residue. The acidic-α-amino acid residue is exemplified by amino acid residues having an acidic group, such as a carboxyl group, a sulfonyl group or a tetrazolyl group, in the side chain thereof. Such amino acid residues include glutamic acid, aspartic acid, cysteic acid, homocysteic acid, β-(5-tetrazolyl)alanine and 2-amino-4-(5-tetrazolyl)butyric acid. Glutamic acid, aspartic acid and cysteic acid are preferred, with greater preference given to aspartic acid. The acidic-α-amino acid residue for Y includes the D-, L- and DL-configurations, with preference given to the L-configuration.

With respect to formula (I) above, C represents an L-α-amino acid residue. The L-α-amino acid residue is exemplified by glycine, L-alanine, L-valine, L-norvaline, L-leucine, L-isoleucine, L-tertiary leucine, L-norleucine, L-methionine, L-2-aminobutyric acid, L-serine, L-threonine, L-phenylalanine, L-aspartic acid, L-glutamic acid, L-asparagine, L-glutamine, L-lysine, L-tryptophan, L-arginine, L-tyrosine and L-proline residues. Of these residues, glycine, L-alanine, L-valine, L-norvaline, L-leucine, L-isoleucine, L-tertiary leucine, L-norleucine, L-methionine, L-2-aminobutyric acid, L-serine, L-threonine, L-aspartic acid, L-glutamic acid, L-asparagine, L-glutamine, L-lysine, L-arginine residues, etc. are preferred, with greater preference given to L-valine, L-norvaline, L-leucine, L-isoleucine, L-tertiary isoleucine, L-norleucine, L-2-aminobutyric acid residues etc., with still greater preference given to L-leucine residue. The α-imino group of these L-α-amino acids may be substituted for by a $C_{1-6}$ alkyl group (e.g., methyl, ethyl, n-propyl, isopropyl, n-butyl, isobutyl, tertiary butyl). Such L-α-amino acids include L-N-methylleucine, L-N-methylnorleucine and L-N (α)-methyltryptophan.

With respect to formula (I) above, $R^1$ in —Asp($R^1$)- represents a group represented by the formula:

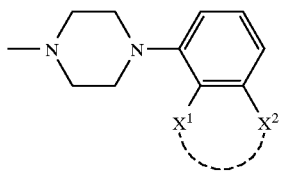

wherein $X^1$ and $X^2$ independently represent a hydrogen atom, a $C_{1-6}$ alkyl group, a $C_{1-6}$ alkoxy group, a halogen atom or a nitro group, and may bind together to form a ring in cooperation with the adjacent carbon atom. Here, $R^1$ is bound to the carbonyl group of the P-carboxyl group of the aspartic acid residue.

The $C_{1-6}$ alkyl group for $X^1$ or $X^2$ is exemplified by methyl, ethyl, n-propyl, isopropyl, n-butyl, isobutyl, tert-butyl, n-pentyl and n-hexyl. $C_{1-3}$ alkyl groups, such as methyl, ethyl, n-propyl and isopropyl, are preferred, with greater preference given to methyl. The $C_{1-6}$ alkoxy group for $X^1$ or $X^2$ is exemplified by methoxy, ethoxy, n-propoxy, n-butoxy, n-pentyloxy and n-hexyloxy. $C_{1-3}$ alkoxy groups, such as methoxy, ethoxy and n-propoxy, are preferred, with greater preference given to methoxy and ethoxy.

The halogen atom for $X^1$ or $X^2$ is exemplified by fluoro, chloro, bromo and iodo, with preference given to chloro.

Concerning the combination of $X^1$ and $X^2$, it is preferable that $X^2$ be a hydrogen atom.

When $X^1$ and $X^2$ bind together to form a ring in cooperation with the adjacent carbon atom, $R^1$ is exemplified by groups represented by the formula:

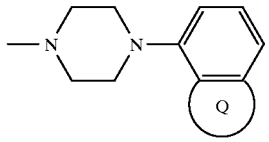

wherein ring Q is exemplified by 4- to 7-membered rings (e.g., saturated carbon rings, aromatic carbon rings, saturated heterocyclic rings, aromatic heterocyclic rings) that may contain about 1 to 3 hetero atoms, such as O, N and S.

Specifically, $R^1$ is exemplified by groups represented by the formula:

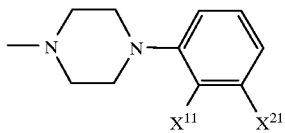

wherein $X^{11}$ and $X^{21}$ independently represent a hydrogen atom, a $C_{1-6}$ alkyl group, a $C_{1-6}$ alkoxy group, a halogen atom or a nitro group), groups represented by the formula:

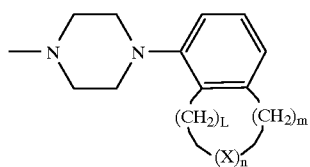

wherein L and m independently represent an integer from 1 to 3; X represents O, S or NH; n represents 0 or 1, groups represented by the formula:

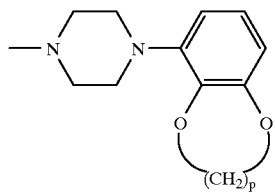

wherein p represents an integer from 1 to 3, and groups represented by the formula:

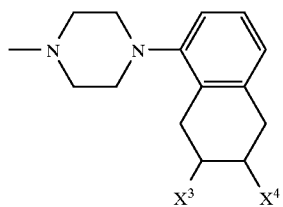

wherein $X^3$ and $X^4$ independently represent a hydrogen atom, a $C_{1-6}$ alkyl group, a $C_{1-6}$ alkoxy group, a halogen atom or a nitro group.

The $C_{1-6}$ alkyl group for $X^{11}$, $X^{21}$, $X^3$ or $X^4$ above is exemplified by methyl, ethyl, n-propyl, isopropyl, n-butyl, isobutyl, tert-butyl, n-pentyl and n-hexyl. $C_{1-3}$ alkyl groups, such as methyl, ethyl, n-propyl and isopropyl are preferred, with greater preference given to methyl. The $C_{1-6}$ alkoxy group for $X^{11}$, $X^{21}$, $X^3$ or $X^4$ above is exemplified by methoxy, ethoxy, n-propoxy, n-butoxy, n-pentyloxy and n-hexyloxy. $C_{1-3}$ alkoxy groups, such as methoxy, ethoxy and n-propoxy, are preferred, with greater preference given to methoxy and ethoxy. The halogen atom for $X^{11}$, $X^{21}$, $X^3$ or $X^4$ above is exemplified by fluoro, chloro, bromo and iodo, with preference given to chloro. Concerning the combination of $X^{11}$ and $X^{21}$, it is preferable that $X^{21}$ be a hydrogen atom; concerning the combination of $X^3$ and $X^4$, it is preferable that $X^4$ be a hydrogen atom.

It is preferable that L be 1 or 2 and m be 1 or 2, and that the sum of L and m be 2 or 3.

Specifically, $R^1$ above is exemplified by the following:

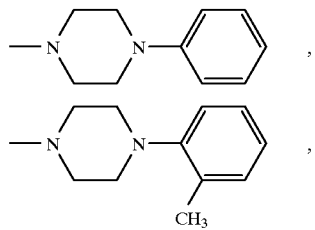

-continued

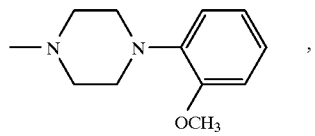

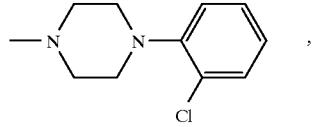

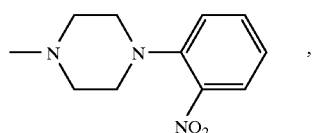

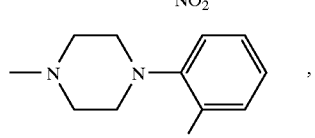

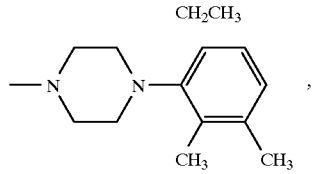

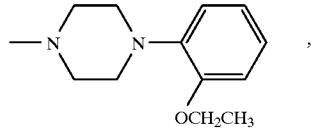

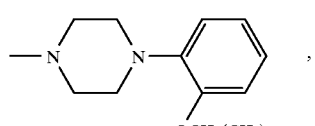

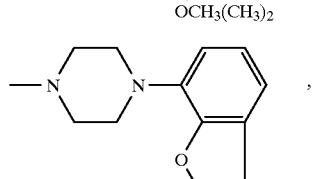

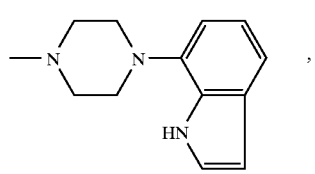

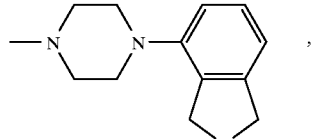

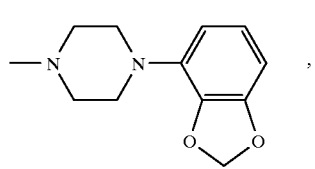

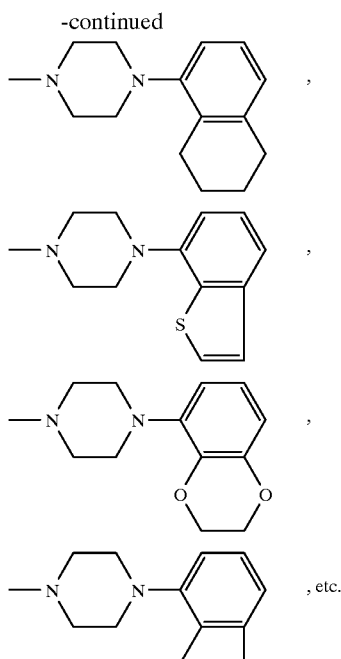

Of these groups, those represented by the formula:

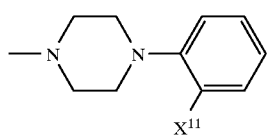

wherein $X^{11}$ represents a hydrogen atom, a $C_{1-6}$ alkyl group, a $C_{1-6}$ alkoxy group, a halogen atom or a nitro group, are preferred, including the following:

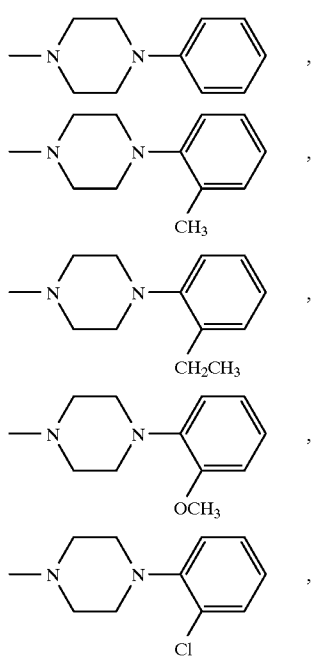

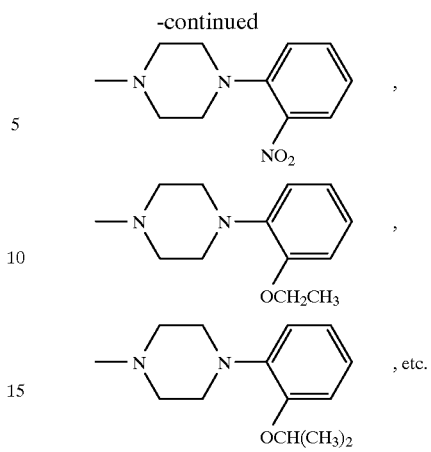

The above group —Asp($R^1$)— includes the D-, L- and DL-configurations, with preference given to the L-configuration.

With respect to formula (I) above, $R^2$ in —NH—CHR$^2$—CO— represents a $C_{1-6}$ alkyl group, a $C_{3-7}$ cycloalkyl group, a $C_{3-7}$ cycloalkyl-$C_{1-3}$ alkyl group, a $C_{1-6}$ alkylthio-$C_{1-3}$ alkyl group, a $C_{3-7}$ cycloalkylthio-$C_{1-3}$ alkyl group, a $C_{1-5}$ alkoxy-$C_{1-3}$ alkyl group, a $C_{3-7}$ cycloalkoxy-$C_{1-3}$ alkyl group, a $C_{1-6}$ alkylthio group, a $C_{3-7}$ cycloalkylthio group, a $C_{1-5}$ alkoxy group or a $C_{3-7}$ cycloalkoxy group.

The $C_{1-6}$ alkyl group for $R^2$ is exemplified by methyl, ethyl, n-propyl, isopropyl, n-butyl, isobutyl, (1-methyl)propyl, tert-butyl, n-pentyl, (2-methyl)butyl, (3-methyl)butyl, neopentyl, n-hexyl, (2,2-dimethyl)butyl and (3,3-dimethyl)butyl, with preference given to $C_{4-6}$ alkyl groups, such as n-butyl, isobutyl, (1-methyl)propyl, tert-butyl, n-pentyl, (2-methyl)butyl, (3-methyl)butyl, neopentyl and n-hexyl.

The $C_{3-7}$ cycloalkyl group for $R^2$ is exemplified by cyclopropyl, cyclobutyl, cyclopentyl, cyclohexyl and cycloheptyl, with preference given to $C_{5-7}$ cycloalkyl groups, such as cyclopentyl, cyclohexyl and cycloheptyl.

The $C_{3-7}$ cycloalkyl-$C_{1-3}$ alkyl group for $R^2$ is exemplified by cyclopropylmethyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, cycloheptylmethyl and cycloheptylethyl, with preference given to $C_{3-7}$ cycloalkylmethyl groups, such as cyclopropylmethyl, cyclobutylmethyl, cyclopentylmethyl, cyclohexylmethyl and cycloheptylmethyl.

The $C_{1-6}$ alkylthio-$C_{1-3}$ alkyl group for $R^2$ is exemplified by methylthiomethyl, methylthioethyl, methylthiopropyl, ethylthiomethyl, ethylthioethyl, n-propylthiopropyl, isopropylthiomethyl, n-butylthiomethyl, tert-butylthiomethyl, n-butylthioethyl, tert-butylthiopropyl and (1,1-dimethyl)propylthiomethyl, with preference given to $C_{4-7}$ alkylthio-methyl groups, such as isopropylthiomethyl, n-butylthiomethyl, tert-butylthiomethyl and (1,1-dimethyl)propylthiomethyl.

The $C_{3-7}$ cycloalkylthio-$C_{1-3}$ alkyl group for $R^2$ is exemplified by cyclopropylthiomethyl, cyclopropylthioethyl, cyclopropylthiopropyl, cyclobutylthiomethyl, cyclobutylthioethyl, cyclobutylthiopropyl, cyclopentylthiomethyl, cyclopentylthioethyl, cyclohexylthiomethyl and cycloheptylthiomethyl, with preference given to $C_{4-7}$ cycloalkylthio-methyl groups, such as cyclobutylthiomethyl, cyclopentylthiomethyl, cyclohexylthiomethyl and cycloheptylthiomethyl.

The $C_{1-6}$ alkoxy-$C_{1-3}$ alkyl group for $R^2$ is exemplified by methoxymethyl, methoxyethyl, methoxypropyl, ethoxymethyl, ethoxyethyl, n-propoxymethyl, n-propoxyethyl, isopropoxymethyl, isopropoxyethyl, n-butoxymethyl, n-butoxyethyl, tert-butoxymethyl, tert-butoxyethyl, n-pentyloxymethyl, n-pentyloxyethyl, (1,1-dimethyl)propoxymethyl, (1,1-dimethyl)propoxyethyl, n-hexyloxymethyl and n-hexyloxyethyl. $C_{1-6}$ alkoxymethyl groups, such as methoxymethyl, ethoxymethyl, n-propoxymethyl, isopropoxymethyl, n-butoxymethyl, tert-butoxymethyl, n-pentyloxymethyl and (1,1-dimethyl) propoxymethyl, are preferred, with greater preference given to isopropoxymethyl, tert-butoxymethyl, (1,1-dimethyl) propoxymethyl and n-hexyloxymethyl.

The $C_{3-7}$ cycloalkoxy-$C_{1-3}$ alkyl group for $R^2$ is exemplified by cyclopropoxymethyl, cyclopropoxyethyl, cyclobutoxymethyl, cyclobutoxyethyl, cyclopentyloxymethyl, cyclopentyloxyethyl, cyclohexyloxymethyl and cycloheptyloxymethyl, with preference given to $C_{3-7}$ cycloalkoxy-methyl groups, such as cyclopropoxymethyl, cyclobutoxymethyl, cyclopentyloxymethyl, cyclohexyloxymethyl and cycloheptyloxymethyl.

$C_{1-6}$ alkylthio group for $R^2$ is exemplified by methylthio, ethylthio, n-propylthio, isopropylthio, n-butylthio, tert-butylthio, n-pentylthio, (1,1-dimethyl)propylthio and n-hexylthio, with preference given to $C_{3-6}$ alkylthio groups, such as n-propylthio, isopropylthio, n-butylthio, tert-butylthio, n-pentylthio, (1,1-dimethyl)propylthio and n-hexylthio.

The $C_{3-7}$ cycloalkylthio group for $R^2$ is exemplified by cyclopropylthio, cyclobutylthio, cyclopentylthio, cyclohexylthio and cycloheptylthio, with preference given to $C_{4-7}$ cycloalkylthio groups, such as cyclobutylthio, cyclopentylthio, cyclohexylthio and cycloheptylthio.

The $C_{1-6}$ alkoxy group for $R^2$ is exemplified by methoxy, ethoxy, n-propoxy, isopropoxy, n-butoxy, tert-butoxy, n-pentyloxy, (1,1-dimethyl)propoxy and n-hexyloxy, with preference given to $C_{3-6}$ alkoxy groups, such as n-propoxy, isopropoxy, n-butoxy, tert-butoxy, n-pentyloxy, (1,1-dimethyl)propoxy and n-hexyloxy.

The $C_{3-7}$ cycloalkoxy group for $R^2$ is exemplified by cyclopropoxy, cyclobutoxy, cyclopentyloxy, cyclohexyloxy and cycloheptyloxy, with preference given to $C_{4-7}$ cycloalkoxy groups, such as cyclobutoxy, cyclopentyloxy, cyclohexyloxy and cycloheptyloxy.

Preferable groups for $R^2$ include $C_{1-6}$ alkyl groups. Specifically, $C_{4-6}$ alkyl groups (e.g., n-butyl, isobutyl, (1-methyl)propyl, tert-butyl, n-pentyl, (2-methyl)butyl, (3-methyl)butyl, neopentylt n-hexyl) are preferred, with greater preference given to tert-butyl and neopentyl, in particular neopentyl.

The α-amino acid residue represented by —NH—CHR$^2$—CO— above includes the D-, L- and DL-configurations, with preference given to the D-configuration.

With respect to formula (I) above, $R^3$ in —D—Trp($N^{in}$—$R^3$)— represents a hydrogen atom, a $C_{1-6}$ alkyl group, a $C_{3-7}$ cycloalkyl group, —COR$^4$ ($R^4$ represents a hydrogen atom, a $C_{1-6}$ alkyl group, a $C_{6-15}$ aryl group or a $C_{6-15}$ aryl-$C_{1-3}$ alkyl group), —COOR$^5$ ($R^5$ represents a $C_{1-6}$ alkyl group, a $C_{6-15}$ aryl group or a $C_{6-15}$ aryl-$C_{1-3}$ alkyl group) or —CONHR$^6$ ($R^6$ represents a hydrogen atom, a $C_{1-6}$ alkyl group, a $C_{6-15}$ aryl group or a $C_{6-15}$ aryl-$C_{1-3}$ alkyl group). Here, $R^3$ is bound to the N atom of the indole group of the tryptophan residue.

The $C_{1-6}$ alkyl group for $R^3$ is exemplified by methyl, ethyl, n-propyl, isopropyl, n-butyl, isobutyl, (1-methyl) propyl, tert-butyl, n-pentyl, (2-methyl)butyl, (3-methyl) butyl, neopentyl, n-hexyl, (2,2-dimethyl)butyl and (3,3-dimethyl)butyl, with preference given to $C_{1-3}$ alkyl groups, such as methyl, ethyl, n-propyl and isopropyl.

The $C_{3-7}$ cycloalkyl group for $R^3$ is exemplified by cyclopropyl, cyclobutyl, cyclopentyl, cyclohexyl and cycloheptyl, with preference given to $C_{5-7}$ cycloalkyl groups, such as cyclopentyl, cyclohexyl and cycloheptyl.

The $C_{1-6}$ alkyl group for $R^4$, $R^5$ or $R^6$ is exemplified by methyl, ethyl, n-propyl, isopropyl, n-butyl, isobutyl, (1-methyl)propyl, tert-butyl, n-pentyl, (2-methyl)butyl, (3-methyl)butyl, neopentyl, n-hexyl, (2,2-dimethyl)butyl and (3,3-dimethyl)butyl, with preference given to $C_{1-3}$ alkyl groups, such as methyl, ethyl, n-propyl and isopropyl.

The $C_{6-15}$ aryl group for $R^4$, $R^5$ or $R^6$ is exemplified by phenyl, α-naphthyl and P-naphthyl, with preference given to phenyl.

The $C_{6-15}$ aryl-$C_{1-3}$ alkyl group for $R^4$, $R^5$ or $R^6$ is exemplified by benzyl, phenylethyl, phenylpropyl, α-naphthylmethyl, α-naphthylethyl, α-naphthylpropyl, β-naphthylmethyl, β-naphthylethyl and β-naphthylpropyl, with preference given to $C_{6-15}$ arylmethyl groups, such as benzyl, α-naphthylmethyl and β-naphthylmethyl.

Specifically, —COR$^4$ is exemplified by formyl, acetyl, propionyl, butyryl, isobutyryl, isovaleryl, pivaloyl, n-pentylcarbonyl, benzoyl and phenylacetyl; —COOR$^5$ is exemplified by methoxycarbonyl, ethoxycarbonyl, phenoxycarbonyl and benzyloxycarbonyl; —CONHR$^6$ is exemplified by carbamoyl, methylaminocarbonyl, ethylaminocarbonyl, n-propylaminocarbonyl, isopropylaminocarbonyl, n-butylaminocarbonyl, isobutylaminocarbonyl, phenylaminocarbonyl and benzylaminocarbonyl.

Preferable groups for $R^3$ include the hydrogen atom and —COR$^4$ ($R^4$ represents a hydrogen atom, a $C_{1-6}$ alkyl group, a $C_{6-15}$ aryl group or a $C_{6-15}$ aryl-$C_{1-3}$ alkyl group). Specifically, the hydrogen atom, formyl group, acetyl group etc. are preferred.

With respect to formula (I) above, when $X^1$ and $X^2$ in $R^1$ are both hydrogen atoms and $R^3$ is a hydrogen atom, $R^2$ is not an isobutyl group. The cyclic hexapeptide having a hydrogen atom for $X^1$ and $X^2$ in $R^1$ and for $R^3$ and an isobutyl group for $R^2$ is produced in Example 70 of EP0528312A2.

Of the cyclic hexapeptides represented by the formula (I) or salts thereof of the present invention, preference is given to those represented by the formula:

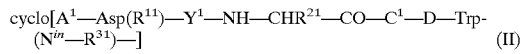

$$\text{cyclo}[A^1—\text{Asp}(R^{11})—Y^1—\text{NH}—\text{CHR}^{21}—\text{CO}—C^1—D—\text{Trp-}(N^{in}—R^{31})—] \qquad (II)$$

wherein $A^1$ represents a D-glutamic acid, D-aspartic acid, D-cysteic acid, D-homocysteic acid, D-β-(5-tetrazolyl) alanine or D-2-amino-4-(5-tetrazolyl)butyric acid residue; $Y^1$ represents a glutamic acid, aspartic acid, cysteic acid, homocysteic acid, β-(5-tetrazolyl)alanine or 2-amino-4-(5-tetrazolyl)butyric acid residue; $C^1$ is a glycine, L-alanine, L-valine, L-norvaline, L-leucine, L-isoleucine, L-tertiary isoleucine, L-norleucine, L-methionine, L-2-aminobutyric acid, L-serine, L-threonine, L-phenylalanine, L-aspartic acid, L-glutamic acid, L-asparagine, L-glutamine, L-lysine, L-tryptophan, L-arginine, L-tyrosine, L-proline, L-N-methylleucine, L-N-methylnorleucine or L-N(α)-methyltryptophan residue; $R^{11}$ represents a group represented by the formula:

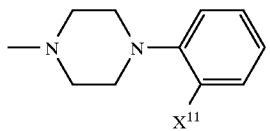

wherein $X^{11}$ represents a hydrogen atom, a $C_{1-6}$ alkyl group, a $C_{1-6}$ alkoxy group, a halogen atom or a nitro group); $R^{21}$ represents a $C_{1-6}$ alkyl group; $R^{31}$ represents a hydrogen atom or —$COR^{41}$ ($R^{41}$ represents a hydrogen atom or a $C_{1-6}$ alkyl group); when $X^{11}$ and $R^{31}$ are both hydrogen atoms, $R^{21}$ is not an isobutyl group, or a salt thereof.

With respect to formula (II) above, the $C_{1-6}$ alkyl group, $C_{1-6}$ alkoxy group or halogen atom for $X^{11}$ is exemplified by the same groups as specified for $X^1$ above. The $C_{1-6}$ alkyl group for $R^{21}$ is exemplified by the same groups as specified for $R^2$ above. The $C_{1-6}$ alkyl group for $R^{41}$ is exemplified by the same groups as specified for $R^4$ above.

It is preferable that $A^1$ be a D-aspartic acid residue, $B^1$ be an aspartic acid residue, $C^1$ be an L-leucine residue, $X^{11}$ be a hydrogen atom or a $C_{1-6}$ alkoxy group, $R^{21}$ be a $C_{4-6}$ alkyl group, and $R^{31}$ be a hydrogen atom or —$COR^{41}$ ($R^{41}$ is a hydrogen atom or a $C_{1-3}$ alkyl group).

The cyclic hexapeptide represented by the formula (I) or a salt thereof of the present invention, is exemplified by:
cyclo[—D—Asp—L—Asp(B1)—L—Asp—D—γMeLeu—L—Leu—D—Trp—],
cyclo[—D—Asp—L—Asp(B7)—L—Asp—D—γMeLeu—L—Leu—D—Trp—] and
cyclo[—D—Asp—L—Asp(B7)—L—Asp—D—γMeLeu—L—Leu—D—Trp(Ac)—].

Salts (or pharmacologically acceptable salts) of the cyclic hexapeptide (I) of the present invention include metal salts (e.g., sodium salt, potassium salt, calcium salt, magnesium salt, zinc salt), salts with bases or basic compounds (e.g., ammonium salt, arginine salt), inorganic acid adduct salts (e.g., hydrochloride, sulfate, phosphate) and organic acid salts (e.g., acetate, propionate, citrate, tartrate, malate, oxalate).

Abbreviations for amino acids, peptides and others used in the present specification are based on abbreviations specified by the IUPAC-IUB Commission on Biochemical Nomenclature or abbreviations in common use in relevant fields. Some examples are given below.
Gly: Glycine
Sar: Sarcosine (N-methylglycine)
Ala: Alanine
Val: Valine
Nva: Norvaline
Ile: Isoleucine
aIle: Alloisoleucine
Nle: Norleucine
Leu: Leucine
N-MeLeu: N-methylleucine
tLeu: Tertiary leucine
γMeLeu: Gamma methylleucine
Met: Methionine
Arg: Arginine
Arg(Tos): Ng-p-toluenesulfonylarginine (g is a superscript)
Lys: Lysine
Lys(Mtr): N($\epsilon$)-(4-methoxy-2,3,6-trimethylbenzenesulfonyl)lysine
Orn: Ornithine
Orn(COPh): N(δ)-benzoylornithine
Orn(COCH$_2$Ph): N(δ)-phenylacetylornithine
Orn(COCH$_2$CH2Ph): N(δ)-(3-phenylpropionyl)ornithine
Orn(COCH$_2$—Ind): N(δ)-({indol-3-yl}acetyl)ornithine
His: Histidine
His(Bom): N(π)-benzyloxymethylhistidine
His(Bzl): N(π)-benzylhistidine
Asp: Aspartic acid
Asn(CH$_2$Ph): N$^4$-benzylasparagine
Asn(CH$_2$CH$_2$Ph): N$^4$-phenethylasparagine
Asn(CH$_2$CH$_2$—Ind): N$^4$-(2-{indol-3-yl}ethyl)asparagine
Asn (Me.CH$_2$CH$_2$Ph): N$^4$-methyl-N$^4$-phenethylasparagine
Asn(CH2CHMePh): N$^4$-({2-phenyl}propyl)asparagine
Asp(B1): Aspartic acid β-4-phenylpiperazine amide
Asp(B2): Aspartic acid β-4-phenylpiperidine amide
Asp(B3): Aspartic acid β-indoline amide
Asp(B4): Aspartic acid β-1-aminoindane amide
Asp(B5): Aspartic acid β-1-aminotetrahydronaphthalene amide
Asp(B6): Aspartic acid β-4-acetylpiperazine amide
Asp(B7): Aspartic acid β-4-(2-methoxyphenyl)piperazine amide
Glu: Glutamic acid
Gln(CH$_2$Ph): N$^5$-benzylglutamine
Gln(CH$_2$CH$_2$Ph): N$^5$-phenethylglutamine
Gln(CH$_2$CH$_2$—Ind): N$^5$-(2-{indol-3-yl}ethyl)glutamine
Glu(B3): Glutamic acid γ-indoline amide
Glu(B4): Glutamic acid γ-1-aminoindane amide
Glu(B5): Glutamic acid γ-1-aminotetrahydronaphthalene amide
Cys: Cysteine
Cta: Cysteic acid
Ser: Serine
Ser(Bzl): O-benzylserine
Thr: Threonine
Thr(Bzl): O-benzylthreonine
Pro: Proline
Tpr: Thioproline
Hyp: 4-hydroxyproline
Hyp(Bzl): 4-benzyloxyproline
Azc: Azetidine-2-carboxylic acid
Pip: Pipecolic acid (piperidine-2-carboxylic acid)
Phe: Phenylalanine
N-MePhe: N-methylphenylalanine
Tyr: Tyrosine
Trp: Tryptophan
mTrp: 5-methyltryptophan
N-MeTrp: N($\alpha$)-methyltryptophan
Trp(Me): Nin-methyltryptophan
Trp(For): Nin-formyltryptophan
Trp(Ac): Nin-acetyltryptophan
Phg: Phenylglycine
Nal(1): 3-(1-naphthyl)alanine
Nal(2): 3-(2-naphthyl)alanine
Thi: 3-(2-thienyl)alanine
Thg(2): 2-(2-thienyl)glycine
Thg(3): 2-(3-thienyl)glycine
Acpr: 1-aminocyclopropane-1-carboxylic acid
Acbu: 1-aminocyclobutane-1-carboxylic acid
Acpe: 1-aminocyclopentane-1-carboxylic acid
Achx: 1-aminocyclohexane-1-carboxylic acid
Achp: 1-aminocycloheptane-1-carboxylic acid
Tic: Tetrahydroisoquinoline-2-carboxylic acid
Cpg: Cyclopentylglycine
The protecting groups and reagents often used in the present specification are symbolized as follows:
AcOEt: Ethyl acetate
Boc: Tertiary butoxycarbonyl
Bzl: Benzyl
BrZ: 2-bromobenzyloxycarbonyl Clz: 2-chlorobenzyloxycarbonyl
Tos: p-toluenesulfonyl
For: Formyl
OBzl: Benzyl ester
OPac: Phenacyl ester
ONB: HONB ester
TFA: Trifluoroacetic acid
TEA: Triethylamine
DIEA: Diisopropylethylamine
IBCF: Isobutyl chloroformate
DMF: N,N-dimethylformamide
DCC: N,N'-dicyclohexylcarbodiimide
DCU: N,N'-dicyclohexylurea
HONB: N-hydroxy-5-norbornane-2,3-dicarboxyimide
HOBt: N-hydroxybenzotriazole
DCM: Dichloromethane
THF: Tetrahydrofuran

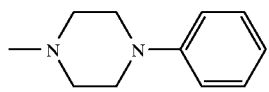
B1

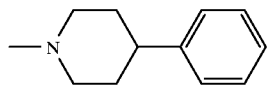
B2

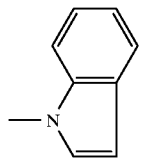
B3

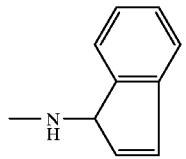
B4

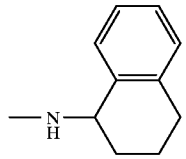
B5

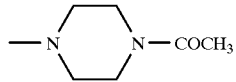
B6

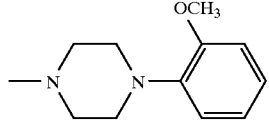
B7

The cyclic hexapeptide represented by the formula (I) or a salt thereof of the present invention, can be produced using an ordinary means of peptide synthesis. Although this production can be achieved by liquid phase synthesis or solid phase synthesis, the former is preferred in some cases. Any optionally chosen known method can be used for this peptide synthesis. Such methods include those described by M. Bodansky and M. A. Ondetti in Peptide Synthesis, Interscience Publishers, N.Y. (1966), by F. M. Finn and K. Hofmann in The Proteins, Vol. 2, edited by H. Nenrath and R. L. Hill, Academic Press Inc., N.Y. (1976), by Nobuo Izumiya et al. in Peptide Gosei No Kiso To Jikken (in Japanese), Maruzen (1985), by H. Yajima, S. Sakakibara et al. in Seikagaku Jikken Koza 1, edited by the Japanese Biochemical Society, Tokyo Kagaku Dojin (1977), by T. Kimura et al. in Zoku Seikagaku Jikken Koza 2, edited by the Japanese Biochemical Society, Tokyo Kagaku Dojin (1987), and by J. M. Stewart and J. D. Young in Solid Phase Peptide Synthesis, Pierce Chemical Company, Ill. (1984), respectively known as the azide method, the chloride method, the acid anhydride method, the mixed acid anhydride method, the DCC method, the active ester method, the method using Woodward reagent K, the carbonylimidazole method, the oxidation reduction method, the DCC/HONB method, and the method using BOP reagent. For example, a cyclic hexapeptide of the formula (I) or a salt thereof can be produced by condensing a starting material having a reactive carboxyl group, which corresponds to one of two fragments of a cyclic hexapeptide represented by the formula:

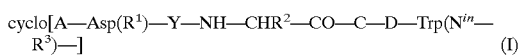

wherein A, Y, C, $R^1$, and $R^3$ have the same definitions as above, divided at optionally chosen positions, and another starting material having a reactive amino group, which corresponds to the other fragment, and cyclizing and condensing the resulting linear hexapeptide, by a known condensing method. When the resulting condensation product has a protecting group, the protecting group is eliminated by a conventional method. In solid synthesis, in particular, the cyclic hexapeptide of the formula (I) or a salt thereof can be produced by binding a n amino acid having a protected functional group not involved in the reaction and an insoluble carrier, such as Pam resin, via the carboxyl group of the amino acid, eliminating the amino-protecting group, then condensing the product with an amino acid having a protected functional group not involved in the reaction, repeating this cycle until the desired protected peptide is obtained, followed by protecting-group elimination by a conventional means, such as treatment with hydrogen fluoride, trifluoromethanesulfonic acid or trifluoroacetic acid, and simultaneous breakage of the bond with the insoluble carrier.

The first and second starting materials mentioned above are normally amino acids and/or peptide fragments; when they are bound together, the desired cyclic hexapeptide of the formula (I) or a salt thereof is formed. The starting amino acids or peptide fragments are normally linear or branched. The "reactive carboxyl group" is defined as the carboxyl group as such, or as activated. The "reactive amino group" is defined as the amino group as such, or as activated. Usually, one of the above two functional groups involved in condensation has been activated. Said carboxyl group and amino group not involved in the condensing reaction were protected before initiation of the condensing reaction.

With respect to the protection of functional groups not involved in the starting material reaction, the protecting groups used, elimination of the protecting groups, activation of the functional groups involved in the reaction etc., known functional groups or known means can be chosen as appropriate.

Protecting groups for the amino group of the starting material include benzyloxycarbonyl, tertiary butyloxycarbonyl, tertiary amyloxycarbonyl, isobornyloxycarbonyl, 4-methoxybenzyloxycarbonyl, 2-chlorobenzyloxycarbonyl, adamantyloxycarbonyl, trifluoroacetyl, phthalyl, formyl, 2-nitrophenylsulfenyl, diphenylphosphonothioyl and 9-fluorenylmethyloxycarbonyl. Protecting groups for the carboxyl group include alkyl esters (e.g., ester groups of methyl, ethyl, propyl, butyl, tertiary butyl, cyclopentyl, cyclohexyl, cycloheptyl, cyclooctyl and 2-adamantyl), benzyl ester, 4-nitrobenzyl ester, 4-methoxybenzyl ester, 4-chlorobenzyl ester, benzhydryl ester, phenacyl ester, benzyloxycarbonylhydrazide, tertiary butyloxycarbonylhydrazide and tritylhydrazide.

Protecting groups for the cysteine thiol group include 4-methoxybenzyl, 4-methylbenzyl, benzyl, tertiary butyl, adamantyl, trityl, acetamidomethyl, carbomethoxysulfenyl, 3-nitro-2-pyridinesulfenyl and trimethylacetamidomethyl.

The hydroxyl group of serine can be protected by, e.g., esterification or etherification. Groups suitable for this esterification include lower alkanoyl groups such as the acetyl group, alloyl groups such as the benzoyl group, and groups derived from carbonic acid, such as the benzyloxycarbonyl group and the ethyloxycarbonyl group. Groups suitable for this etherification include the benzyl group, the tetrahydropyranyl group and the tertiary butyl group. However, the hydroxyl group of serine may not be protected.

Protecting groups for the phenolic hydroxyl group of tyrosine include benzyl, 2,6-dichlorobenzyl, 2-nitrobenzyl, 2-bromobenzyloxycarbonyl and tertiary butyl. However, the phenolic hydroxyl group of tyrosine may not be protected.

Methionine may be protected in the form of a sulfoxide.

Protecting groups for the imidazole of histidine include p-toluenesulfonyl, 4-methoxy-2,3,6-trimethylbenzenesulfonyl, 2,4-dinitrophenyl, benzyloxymethyl, tertiary butoxymethyl, tertiary butoxycarbonyl, trityl and 9-fluorenylmethyloxycarbonyl. However, the imidazole of histidine may not be protected.

Protecting groups for the indole of tryptophan include formyl, 2,4,6-trimethylbenzenesulfonyl, 2,4,6-trimethoxybenzenesulfonyl, 4-methoxy-2,3,6-trimethylbenzenesulfonyl, 2,2,2-trichloroethyloxycarbonyl and diphenylphosphonothioyl. However, the indole of tryptophan may not be protected.

Starting materials having an activated carboxyl group include corresponding acid anhydrides, azides and active esters [esters with alcohols (e.g., pentachlorophenol, 2,4,5-trichlorophenol, 2,4-dinitrophenol, cyanomethyl alcohol, p-nitrophenol, N-hydroxy-5-norbornane-2,3-dicarboxyimide, N-hydroxysuccinimide, N-hydroxyphthalimide, N-hydroxybenzotriazole)]. Starting materials having an activated amino group include corresponding phosphoric acid amides.

This condensing reaction can be carried out in the presence of a solvent. The solvent is chosen as appropriate from among solvents known to be useful in peptide condensation. Such solvents include anhydrous or hydrated dimethylformamide, dimethyl sulfoxide, pyridine, chloroform, dioxane, dichloromethane, tetrahydrofuran, acetonitrile, ethyl acetate, N-methylpyrrolidone, and appropriate mixtures thereof. Reaction temperature is chosen as appropriate over the range known to be useful for peptide bond formation reaction, normally about −20 to 30° C.

Intramolecular cyclization can be carried out at any position in the peptide by a known method. For example, the terminal α-carboxyl-protecting group of the C-terminal amino acid of the protected peptide is first eliminated by a known method, followed by activation by a known method, after which the terminal α-amino acid residue of the N-terminal amino acid is eliminated by a known method and the peptide is intramolecularly cyclized at the same time. Alternatively, the terminal α-carboxyl-protecting group of the C-terminal amino acid of the protected peptide and the terminal α-amino-protecting group of the N-terminal amino acid are eliminated at the same time, after which the peptide is intramolecularly cyclized by a known condensing reaction. It is preferable to carry out the intramolecular cyclization under high dilution conditions in some cases.

Useful methods of protecting group elimination include catalytic reduction in a hydrogen stream in the presence of a catalyst such as palladium black or palladium carbon, acid treatment with anhydrous hydrogen fluoride, methanesulfonic acid, trifluoromethanesulfonic acid, trifluoroacetic acid or a mixture thereof, and reduction with sodium in liquid ammonia. In protecting group elimination by the above acid treatment, normally carried out at temperatures between −20 and 40° C., it is effective to add a cation capturing agent, such as anisole, phenol, thioanisole, metacresol, p-cresol, dimethyl sulfide, 1,4-butanediol or 1,2-ethanedithiol. The 2,4-dinitrophenyl group used to protect the imidazole of histidine is eliminated by thiophenol treatment. The formyl group used to protect the indole of tryptophane is eliminated by alkaline treatment, such as with dilute sodium hydroxide or dilute ammonia, as well as by the above-described acid treatment in the presence of 1,2-ethanedithiol, 1,4-butanedithiol or the like.

Cyclic hexapeptide (I) thus produced is collected by ordinary means of peptide separation and purification, such as extraction, distribution, reprecipitation, recrystallization, column chromatography and high performance liquid chromatography, after completion of the reaction.

Cyclic hexapeptide (I) of the present invention can be obtained as a metal salt (e.g., sodium salt, potassium salt, calcium salt, magnesium salt, zinc salt), a salt with a base or basic compound (e.g., ammonium salt, arginine salt), an acid adduct salt, particularly a pharmacologically acceptable acid adduct salt, such as a salt with an inorganic acid (e.g., hydrochloric acid, sulfuric acid, phosphoric acid) or an organic acid (e.g., acetic acid, propionic acid, citric acid, tartaric acid, malic acid, oxalic acid, methanesulfonic acid), by a known method.

The cyclic hexapeptide (I) or a salt thereof of the present invention thus obtained exhibits excellent antagonistic action against endothelin receptors (i.e., both endothelin A receptors and endothelin B receptors), particularly against endothelin B receptors. That is, the cyclic hexapeptide (I) or a salt thereof antagonizes both endothelin A receptors, and endothelin B receptors, more potently antagonizing endothelin B receptors than do conventional endothelin receptor antagonists. Also the cyclic hexapeptide (I) or a salt thereof may antagonize endothelin B receptors, while showing almost no antagonistic action against endothelin A receptors. In other words, the cyclic hexapeptide (I) or a salt thereof is more selective for endothelin receptors, in comparison with conventional endothelin receptor antagonists. Specifically, the cyclic hexapeptide (I) or a salt thereof is characterized by 1) more potent antagonistic action against endothelin B receptors (e.g., lower $IC_{50}$ values), in comparison with the peptide produced in Examples of EP0528312A2, or 2) more potent antagonistic action against endothelin B receptors than against endothelin A receptors (e.g., lower ratios of $IC_{50}$ values for endothelin B receptors/$IC_{50}$ values for endothelin A receptors), in comparison with the peptide produced in Examples given in the specification for EP0528312A2. For example, the cyclic hexapeptide (I) or a salt thereof is equivalent in $IC_{50}$ values for endothelin B receptors and higher in $IC_{50}$ values for endothelin A receptors, in comparison with conventional endothelin receptor antagonists. Therefore, the cyclic hexapeptide (I) or a salt thereof is capable of more efficiently suppressing vascular smooth muscle contractions mediated by endothelin B receptors, in comparison with conventional endothelin receptor antagonists.

Because the cyclic hexapeptide (I) or a salt thereof antagonizes endothelin A receptors, although this antagonistic action is less potent than its antagonistic action against endothelin B receptors, it is capable of suppressing vascular smooth muscle contractions respectively mediated by endothelin A receptors and endothelin B receptors, even when used alone. However, when used in combination with the peptide produced in Examples given in the specification for EP0528312A2, which excellently antagonizes endothelin A receptors, the cyclic hexapeptide (I) or a salt thereof is capable of more effectively suppressing vascular smooth muscle contractions respectively mediated by endothelin A receptors and endothelin B receptors. The cyclic hexapeptide (I) or a salt thereof is therefore useful as an endothelin receptor antagonist (endothelin B receptor antagonist, in particular) in warm-blooded animals (e.g., rats, mice, rabbits, chickens, pigs, sheep, bovines, monkeys, humans). The cyclic hexapeptide (I) or a salt thereof is a safe peptide of low toxicity.

Also, because the cyclic hexapeptide (I) or a salt thereof possesses excellent endothelin antagonistic activity as described above, it can be used as a therapeutic agent for diseases caused by endothelin, such as hypertension, pulmonary hypertension, angina pectoris, myocardiopathy, myocardial infarction, Raynaud's disease, Berger's disease, cerebral infarction, cerebral vascular spasms, asthma, acute renal failure, cyclosporine- or cisplatin-associated renal dysfunction, arteriosclerosis, diabetic nephropathy, diabetic neurosis, diabetic retinopathy, hemorrhagic shock, endotoxin shock, dysfunction of organs (e.g., liver) in organ surgery or transplantation, and hyperlipidemia.

When the cyclic hexapeptide (I) or a salt thereof is non-orally administered as an endothelin antagonist, it is normally used in the form of a liquid (e.g., injection). Injectable preparations include intravenous, subcutaneous, intracutaneous, intramuscular and drip infusion injections. Such injections are prepared by a known method, i.e., by dissolving, suspending or emulsifying a compound possessing endothelin receptor antagonistic action in a sterile aqueous or oily solution. Aqueous solutions for injection include physiological saline, and isotonic solutions containing glucose and other auxiliary agents (e.g., D-sorbitol, D-mannitol, sodium chloride), and may be used in combination with appropriate dissolution aids, such as alcohols (e.g., ethanol), polyalcohols (e.g., propylene glycol, polyethylene glycol), and nonionic surfactants (e.g., polysorbate 80, HCO-50). Oily solutions include sesame oil and soybean oil, and may be used in combination with dissolution aids, such as benzyl benzoate and benzyl alcohol. Buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol) and other additives may also be added. The injection thus prepared is normally packed in an appropriate ampule. The dose per administration is normally about 0.01 to 100 mg, preferably about 0.01 to 50 mg, and more preferably about 0.01 to 20 mg per kg body weight, depending on subject, target organ, symptoms, method of administration and other factors, in the case of an injection; it is advantageous to give this dose by intravenous injection.

For oral administration, the cyclic hexapeptide (I) or a salt thereof is administered in the form of an oral preparation, such as powders, tablets, granules or capsules. In producing such an oral preparation, a pharmaceutically acceptable carrier may be added. Such carriers include excipients (e.g., lactose, starch), lubricants (e.g., magnesium stearate, talc), binders (hydroxypropyl cellulose, hydroxypropylmethyl cellulose, macrogol) and disintegrating agents (e.g., starch, carboxymethyl cellulose calcium). Antiseptics (e.g., benzyl alcohol, chlorobutanol, methyl p-oxybenzoate, propyl p-oxybenzoate), antioxidants, coloring agents, sweetening agents and other additives may also be used as necessary. The dose per administration is normally about 5 mg to 1 g, preferably about 10 to 100 mg per kg body weight.

The cyclic hexapeptide (I) or a salt thereof can also be administered as a sustained-release preparation as disclosed in Japanese Patent Application No. 153393/1993. Specifically, the cyclic hexapeptide (I) or a salt thereof can be administered in a sustained-release preparation along with a biodegradable polymer (e.g., copolymer of fatty acid polyester or glycolic acid and lactose).

[EXAMPLES]

The present invention is hereinafter described in more detail by means of the following examples, which are not to be construed as limitative.

Example 1

Production of cyclo[—D—Asp—Asp(B7)—Asp—D—γMeLeu—L—Leu—D—Trp—]

(1) Production of Boc—D—γMeLeu—OH 4.80 g (33.06 mmole) of H—D—γMeleu—OH (produced by Watanabe Chemical Industries, Ltd.) was dissolved in a mixed solvent of 60 ml of dioxane and 30 ml of water. To this solution, 60 ml of a dioxane solution of 7.94 g (36.4 mmole) of $(Boc)_2O$ and 33.06 ml of a 1M aqueous sodium hydroxide solution were simultaneously added drop by drop at the same rate under ice cooling conditions, followed by overnight stirring. After the reaction mixture was concentrated to 30 ml, 200 ml of water and 200 ml of ethyl acetate were added; the mixture was adjusted to pH about 2 with 6N hydrochloric acid under ice cooling conditions to extract the desired product in the ethyl acetate layer. This extract was twice washed with 100 ml of dilute hydrochloric acid, after which it was washed with water to obtain a nearly neutral pH value and dried over $Na_2SO_4$, and the solvent was distilled off under reduced pressure. Petroleum ether was added to the residue; the resulting precipitate was collected by filtration to yield a white powder.

Yield: 7.08 g (recovery 87.3%)

m.p.: 98–99° C. $Rf_1$: 0.14 $Rf_2$: 0.62

$[\alpha]_D^{25}$: 15.6° (c=1.16, DMF)

Elemental analysis (for $Cl_2H_{23}N_1O_4$):

Calculated: C, 58.75; H, 9.45; N, 5.71

Found: C, 58.96; H, 9.68; N, 5.75

(2) Production of Boc—D—γMeLeu—Leu—OBzl 10.39 g (26.4 mmole) of pTos.H—Leu—OBzl was dissolved in 30 ml of DMF. To this solution, 4.82 ml (27.7 mmole) of diisopropylethylamine was added under ice cooling conditions, after which Boc—D—γMeLeu—ONH (prepared from 6.80 g (27.7 mmole) of Boc—D—γMeLeu—OH as synthesized in (1) above, 5.22 g (29.1 mmole) of HONB and 6.01 g (29.1 mmole) of DCC) was added, followed by overnight stirring. After the solvent was distilled off under reduced pressure, the residue was dissolved in 200 ml of ethyl acetate. This solution was washed with a 10% aqueous citric acid solution, saturated saline, a 4% aqueous NaHCO$_3$ solution and saturated saline, and dried over Na$_2$SO$_4$. After the solvent was distilled off, the residue was recrystallized from petroleum ether to yield a colorless crystal.

Yield: 11.0 g (recovery 92.5%)
m.p.: 93–94° C Rf$_1$: 0.74 Rf$_2$: 0.84
$[\alpha]_D^{25}$: 8.9° (c=1.00, DMF)
Elemental analysis (for C$_{25}$H$_{40}$N$_2$O$_5$):
  Calculated: C, 66.93; H, 8.99; N, 6.24
  Found: C, 66.98; H, 9.00; N, 6.29

(3) Production of Boc—D—γMeLeu—Leu—OPac 10.8 g (24.0 mmole) of Boc—D—γMeLeu—Leu—OBzl as synthesized in (2) above was dissolved in 400 ml of methanol. To this solution, 1 g of palladium black was added, followed by stirring in a hydrogen stream at normal temperature and normal pressure for 5 hours. After the catalyst was filtered off, the solvent was concentrated under reduced pressure to about 100 ml. To this concentrate, 10 ml of an aqueous solution of 3.91 g (12.0 mmole) of Cs$_2$CO$_3$ was added drop by drop over a period of 10 minutes. After additional stirring for 30 more minutes, the solvent was distilled off. To the residue, 50 ml of DMF was added; the solvent was distilled off under reduced pressure. This procedure was twice repeated. The residue was dissolved in 50 ml of DMF. To this solution, 50 ml of a DMF solution of 5.02 g (25.2 mmole) of phenacyl bromide was added drop by drop under ice cooling conditions over a period of 10 minutes, followed by overnight stirring at room temperature. After the solvent was distilled off under reduced pressure, the residue was dissolved in ethyl acetate. This solution was washed with a 10% aqueous citric acid solution, saturated saline, a.4% aqueous NaHCO$_3$ solution and saturated saline, and dried over Na$_2$SO$_4$. After the solvent was distilled off, the residue was crystallized from petroleum ether to yield a colorless crystal.

Yield: 10.9 g (recovery 94.9%)
m.p.: 57–58° C. Rf$_1$: 0.64 Rf$_2$: 0.78
$[\alpha]_D^{25}$: 3.7° (c=1.14, DMF)
Elemental analysis (for C$_{26}$H$_{40}$N$_2$O$_6$):
  Calculated: C, 65.52; H, 8.46; N, 5.88
  Found: C, 65.35; H, 8.65; N, 5.79

(4) Production of Boc—Asp(OBzl)—D—γMeLeu—Leu—OPac

To 10.5 g (22.0 mmole) of Boc—D—γMeLeu—Leu—OPac as synthesized in (3) above, 40 ml of 10 N HCl/dioxane was added, followed by stirring for 15 minutes. After the solvent was distilled off under reduced pressure, ether was added; the resulting precipitate was collected by filtration, and dried. This dry product was dissolved in 30 ml of DMF. While this solution was cooled with ice, 4.02 ml (23.1 mmole) of diisopropylethylamine was added. To this mixture, Boc—Asp(OBzl)—ONB (prepared from 7.83 g (24.2 mmole) of Boc—Asp(OBzl)—OH, 4.77 g (26.6 mmole) of HONB and 5.49 g (26.6 mmole) of DCC) was added, followed by overnight stirring. After the resulting insoluble matter was filtered off, the filtrate was concentrated; the residue was dissolved in ethyl acetate, washed with a 10% aqueous citric acid solution, saturated saline, a 4% aqueous NaHCO$_3$ solution and saturated saline, and dried over Na$_2$SO$_4$. After the solvent was distilled off, the residue was crystallized from ether-petroleum ether to yield a colorless crystal.

Yield: 13.5 g (recovery 90.0%)
m.p.: 123–124° C. Rf$_1$: 0.57 Rf$_2$: 0.76
$[\alpha]_D^{25}$: -19.6° (c=1.19, DMF)
Elemental analysis (for C$_{37}$H$_{51}$N$_3$O$_9$):
  Calculated: C, 65.18; H, 7.54; N, 6.16
  Found: C, 65.10, H, 7.29; N, 6.10

(5) Production of Boc—Asp(B7)—Asp(OBzl)—D—γMeLeu—Leu—OPac 4.12 g (18 mmole) of 1-(2-methoxyphenyl)piperazine (produced by Aldrich) was dissolved in 30 ml of DMF. While this solution was cooled with ice, 10 ml of a DMF solution containing Boc—Asp(ONB)—OBzl (prepared from 4.85 g (15 mmole) of Boc—Asp—OBzl, 2.97 g (16.5 mmole) of HONB and 3.40 g (16.5 mmole) of DCC) was added drop by drop, followed by overnight stirring at room temperature. After the solvent was distilled off under reduced pressure, the residue was dissolved in 50 ml of ethyl acetate. This solution was washed with a 10% aqueous citric acid solution, saturated saline, a 4% aqueous NaHCO$_3$ solution and saturated saline, and dried over Na$_2$SO$_4$. After the solvent was distilled off, the residue was dissolved in 20 ml of a 1:1 mixture of hexane and ethyl acetate, and purified by silica gel column chromatography (5 cm dia.×10 cm, hexane:ethyl acetate=7:3). 1.81 g (3.63 mmole) of the resulting oily Boc—Asp(B7)—OBzl was dissolved in 50 ml of methanol. To this solution, 0.1 g of palladium black was added, followed by stirring in a hydrogen stream at normal temperature and normal pressure for 2 hours. After the catalyst was filtered off, the solvent was distilled off under reduced pressure. The residue was dissolved in 20 ml of acetonitrile and treated with 715 mg (3.99 mmole) of HONB and 824 mg (3.99 mmole) of DCC to yield Boc—Asp(B7)—ONB.

To 1.48 g (3.63 mmole) of Boc—Asp(OBzl)—D—γMeLeu—Leu—OPac as synthesized in (4) above, 20 ml of 10N HCl/dioxane was added under ice cooling conditions, followed by stirring for 15 minutes. After the solvent was distilled off under reduced pressure, ether was added; the resulting precipitate was collected by filtration and dried. This dry product was dissolved in 10 ml of DMF. While this solution was cooled with ice, 0.60 ml (3.47 mmole) of diisopropylethylamine was added. To this mixture, Boc—Asp(B7)—ONB as prepared above was added, followed by overnight stirring. After the resulting insoluble matter was filtered off, the filtrate was concentrated; the residue was dissolved in ethyl acetate. To this solution, 0.27 ml (2.08 mmole) of N,N-dimethyl-1,3-propanediamine was added, followed by stirring for 5 minutes. This mixture was washed with a 10% aqueous citric acid solution, saturated saline, a 4% aqueous NaHCO$_3$ solution and saturated saline, and dried over Na$_2$SO$_4$. After the solvent was distilled off, the residue was precipitated by addition of petroleum ether to yield a white powder.

Yield: 2.65 g (recovery 82.7%)
m.p.: 84–87° C. Rf$_1$: 0.40 Rf$_2$: 0.71
$[\alpha]_D^{25}$: -48.3° (c=1.18, DMF)
Elemental analysis (for C$_{52}$H$_{70}$N$_6$O$_{12}$):
  Calculated: C, 64.31; H, 7.27; N, 8.65
  Found: C, 64.14; H, 7.37; N, 8.71

(6) Production of Boc—D—Asp(OBzl)—Asp(B7)—Asp(OBzl)—D—γMeLeu—Leu—OPac

To 2.50 g (2.58 mmole) of Boc—Asp(B7)—Asp(OBzl)—D—γMeLeu—Leu—OPac as synthesized in (5) above, 20 ml of 10N HCl/dioxane was added under ice cooling conditions, followed by stirring for 15 minutes. After the solvent was distilled off under reduced pressure, ether was added; the resulting precipitate was collected by filtration and dried. This dry product was dissolved in 5 ml of DMF. While this solution was cooled with ice, 0.47 ml (5.42 mmole) of diisopropylethylamine was added. To this mixture, Boc—D—Asp(OBzl)—ONB (prepared from 918 mg (2.84 mmole) of Boc—D—Asp(OBzl)—OH, 559 mg (3.12 mmole) of HONB and 644 mg (3.12 mmole) of DCC) was added, followed by overnight stirring. After the resulting insoluble matter was filtered off, the filtrate was concentrated; the residue was dissolved in ethyl acetate. To this solution, 0.27 ml (2.08 mmole) of N,N-dimethyl-1,3-propanediamine was added, followed by stirring for 5 minutes. This mixture was washed with a 10% aqueous citric acid solution, saturated saline, a 4% aqueous $NaHCO_3$ solution and saturated saline, and dried over $Na_2SO_4$. After the solvent was distilled off, the residue was precipitated with petroleum ether to yield a white powder.

Yield: 2.59 g (recovery 85.3%)

m.p.: 81–83° C. $Rf_1$: 0.40 $Rf_2$: 0.74

$[\alpha]_D^{25}$: −36.9° (c=1.25, DMF)

Elemental analysis (for $C_{63}H_{81}N_7O_{15}$):

Calculated: C, 64.32; H, 6.94; N, 8.33

Found: C, 64.25; H, 7.10; N, 8.28

(7) Production of Boc—D—Trp—D—Asp(OBzl)—Asp(B7)—Asp(OBzl)—D—γMeLeu—Leu—OPac

To 1.18 g (1.00 mmole) of Boc—D—Trp—D—Asp(OBzl)—Asp(B7)—Asp(OBzl)—D—γMeLeu—Leu—OPac as synthesized in (6) above, 20 ml of 10N HCl/dioxane was added under ice cooling conditions, followed by stirring for 15 minutes. After the solvent was distilled off under reduced pressure, ether was added; the resulting precipitate was collected by filtration and dried. This dry product was dissolved in 4 ml of DMF. While this solution was cooled with ice, 0.36 ml (2.10 mmole) of diisopropylethylamine was added. To this mixture, Boc—D—Trp—ONB (prepared from 335 mg (1.10 mmole) of Boc—D—Trp—OH, 217 mg (1.21 mmole) of HONB and 250 mg (1.21 mmole) of DCC) was added, followed by overnight stirring. After the resulting insoluble matter was filtered off, the filtrate was concentrated; the residue was dissolved in ethyl acetate. To this solution, 0.08 ml (0.660 mmole) of N,N-dimethyl-1,3-propanediamine was added, followed by stirring for 5 minutes. This mixture was washed with a 10% aqueous citric acid solution, saturated saline, a 4% aqueous $NaHCO_3$ solution and saturated saline, and dried over $Na_2SO_4$. After the solvent was distilled off, the residue was precipitated by addition of ethyl acetate-petroleum ether to yield a white powder.

Yield: 1.22 g (recovery 89.5%)

m.p.: 94–97° C. $Rf_1$: 0.31 $Rf_2$: 0.64

$[\alpha]_D^{25}$: −22.2° (c=1.08, DMF)

Elemental analysis (for $C_{74}H_{91}N_9O_{16}$):

Calculated: C, 65.23; H, 6.73; N, 9.25

Found: C, 65.04; H, 6.97; N, 9.11

(8) Production of Boc—D—Trp—D—Asp(OBzl)—Asp(B7)—Asp(OBzl)—D—γMeLeu—Leu—OH 1.09 g (0.80 mmole) of Boc—D—Trp—D—Asp(OBzl)—Asp(B7)—Asp(OBzl)—D—γMeLeu—Leu—OPac as synthesized in (7) above was dissolved in 20 ml of a 90% aqueous solution of acetic acid. To this solution, 2.62 g (40 mmole) of zinc powder was added, followed by stirring for 1 hour. After the zinc powder was filtered off, the filtrate was concentrated; the residue was dissolved in dichloromethane, washed with dilute sulfuric acid and saturated saline, and dried over $Na_2SO_4$. After the solvent was distilled off, the residue was precipitated by addition of petroleum ether-ether to yield a white powder.

Yield: 767 mg (recovery 77.0%)

m.p.: 104–106° C. $Rf_1$: 0.18 $Rf_2$: 0.62

$[\alpha]_D^{25}$: −16.6° (c=1.41, DMF)

Elemental analysis (for $C_{66}H_{85}N_9O_{15}$):

Calculated: C, 63.70; H, 6.88; N, 10.13

Found: C, 63.55; H, 6.94; N, 9.99

(9) Production of cyclo[—D—Asp—Asp(B7)—Asp—D—γMeLeu—Leu—D—Trp—]

600 mg (0.48 mmole) of Boc—D—Trp—D—Asp(OBzl)—Asp(B7)—Asp(OBzl)—D—γMeLeu—Leu—OH as synthesized in (8) above was dissolved in 5 ml of DMF. While this solution was cooled with ice, 173 mg (0.96 mmole) of HONB and 199 mg (0.96 mmole) of DCC were added, followed by overnight stirring at 4° C. After the resulting insoluble matter was filtered off, the solvent was distilled off under reduced pressure. To the residue, 5 ml of 10N HCl/dioxane was added under ice cooling conditions, followed by stirring for 15 minutes. After the reaction mixture was concentrated, ether was added to the residue; the resulting precipitate was collected by filtration and dried. This dry product was dissolved in 10 ml of DMF; the solution was added drop by drop to 90 ml of DMF containing 0.42 ml (2.41 mmole) of diisopropylethylamine, followed by stirring at room temperature for 3 hours. After the solvent was distilled off under reduced pressure, the residue was dissolved in ethyl acetate. This solution was washed with a 10% aqueous citric acid solution, saturated saline, a 4% aqueous $NaHCO_3$ solution and saturated saline, and dried over $Na_2SO_4$. After the solvent was distilled off, the residue was precipitated with ether-petroleum ether; the resulting precipitate was collected by filtration. 400 mg of the precipitate was dissolved in 20 ml of DMF. To this solution, 0.1 g of palladium black was added, followed by stirring in a hydrogen stream at normal temperature and normal pressure for 2 hours. After the catalyst was filtered off, the solvent was distilled off under reduced pressure. After addition of water, the residue was lyophilized, to yield 360 mg of a white powder. 68.4 mg of this powder was purified by reverse phase liquid chromatography (column YMC D-ODS-5 (2 cm×25 cm), eluent 0.1% TFA-containing acetonitrile solution (37%–47% acetonitrile linear density gradient/30 minutes). Yield: 22.0 mg (preparatory HPLC recovery 32%) LSIMS $(M+H)^+$=946 (calculated value=946)

Example 2

The following peptide was produced by the method of Example 1.

cyclo(—D—Asp—L—Asp(B1)—L—Asp—D—γMeLeu—L—Leu—D—Trp—)

LSIMS $(M+H)^+$=916 (calculated value=916)

Example 3

The following peptide was produced by the method of Example 1.

cyclo(—D—Asp—L—Asp(B7)—L—Asp—D—γMeLeu—L—Leu—D—Trp(Ac)—)

LSIMS $(M+H)^+$=988 (calculated value=988)

Example 4

Production of cyclo[—D—Asp—Asp(B7)—Asp—D—γMeLeu—Leu—D—Trp—].2Na 4.4 g of cyclo[—D—Asp—Asp(B7)—Asp—D—γMeLeu—D—Trp—] as prepared by the method of Example 1 was dissolved in 50 ml of methanol, concentrated, dissolved in 50 ml of methanol again, and then cooled with ice. To this solution, 46.4 ml of a 0.1N aqueous sodium hydroxide solution was added drop by drop. After addition of a 0.1N aqueous sodium hydroxide solution to obtain pH 7 to 8, the mixture was concentrated; after addition of distilled water, the concentrate was lyophilized.

Elemental analysis (for $C_{47}H_{61}N_9O_{12}Na_2 \cdot CF_3CO_2Na \cdot 0.5CH_3CO_2Na \cdot 3H_2O$):

Calculated: C, 49.18; H, 5.65; N, 10.32
Found: C, 49.08; H, 5.50; N, 10.33

Formulation Example 1

3.6 g of lactic acid-glycolic acid copolymer (lactic acid/ glycolic acid=75/25 mol %, GPC weight-average molecular weight 15,038, GPC number-average molecular weight 5,195, produced by Wako Pure Chemical Industry) was dissolved in 6.6 g (5 ml) of dichloromethane. To this solution was added a solution of peptide as obtained in Example 4 (250 mg) and L-arginine (100 mg) in 0.5 ml of distilled water, and the mixture was stirred for about 30 seconds using a homogenizer (Polytron) to yield a w/o emulsion. The emulsion was injected to 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield a w/o/w emulsion, which was then stirred at a room temperature for 3 hours to volatile the dichloromethane and solidify the oil phase, which was then collected via centrifugation at 2,000 rpm using a centrifuge (05PR-22, Hitachi, Ltd.). The precipitate was again dispersed in distilled water, centrifuged and washed to remove the free drug etc. After 100 mg of D-mannitol was added to the collected microcapsules, the microcapsules were re-dispersed in a small amount of distilled water, and the dispersion was lyophilized to yield powdery microcapsules.

The microcapsules thus obtained were homogenized and extracted in 0.1M ammonium acetate solution containing 30% (v/v) acetonitrile for 3 hours, and then assayed by HPLC (high performance liquid chromatography).

As the result, the content of peptide as obtained in Example 4 was 5.2 mg per 100 mg of microcapsules.

Comparative Formulation 1

Powdery microcapsules were obtained in the same manner as Formulation Example 1, except that the peptide of Example 4 was not used.

Reference Example 1

The following peptide was produced in accordance with Example 96 of EP0528312A2.
cyclo(—D—Asp—L—Asp(B1)—L—Asp—D—Thg(2)—L—Leu—D—Trp—)

Test Example 1
Determination of endothelin receptor binding activity (1) Determination of ETA receptor binding activity A membrane fraction prepared from swine ventricular muscle was diluted to 12 $\mu$g/ml with an assaying buffer and dispensed to assaying tubes at 100 $\mu$l per tube. To this membrane fraction suspension were added 2 $\mu$l of a solution of endothelin-1 labeled with 100 pmole of radioactive iodine ([$^{125}$I]ET-1, produced by Amersham Medical Ltd.) and 3 $\mu$l of a solution of the subject compound at various concentrations, followed by incubation at 25° C. for 1 hour. The suspension was then diluted with an ice-cooled assaying buffer and filtered through a glass filter GF/F (produced by Whatman K.K.). The membrane fraction containing endothelin A (ET$_A$) receptors and receptor-bound [$^{125}$I)ET-1 were recovered on the filter. The radioactivity retained on the filter was measured to obtain the amount of [$^{125}$I]ET-1 bound to the ETA receptors. The amount of [$^{125}$I,]ET-1 bound in the presence of ET-1 in great excess as the test compound was taken as the amount of nonspecific binding. The amount of specific binding (SPB) of [$^{125}$I]ET-1 was obtained by subtracting the amount of nonspecific binding from the total amount of binding determined. The percent SPB value at test compound concentration C (molar concentration by volume) was defined as the percent ratio of the amount of specific binding relative to the amount of specific binding obtained at a test compound concentration of 0. The thus-obtained value was substituted for the following "pseudo-Hill's equation" to calculate the test compound concentration (IC$_{50}$ value) required to have a value of 50% for the amount of specific binding of [125I]ET-1.
log[%SPB/(100 - %SPB)]=n[logC - log(IC$_{50}$)]
   n: Pseudo-Hill's coefficient
(2) Determination of ETB receptor binding activity A membrane fraction prepared from a bovine brain was diluted to 150 $\mu$g/ml with an assaying buffer and dispensed to assaying tubes at 100 $\mu$l per tube. To this membrane fraction suspension were added 2 $\mu$l of a solution of endothelin-1 labeled with 100 pM of radioactive iodine ([$^{125}$I]ET-1, produced by Amersham Medical Ltd.) and 3 $\mu$l of a solution of the subject compound at various concentrations, followed by incubation at 25° C. for 1 hour. The suspension was then diluted with an ice-cooled assaying buffer and filtered through a glass filter GF/F (produced by Whatman K.K.). The membrane fraction containing endothelin B (ET$_B$) receptors and receptor-bound [$^{125}$I)ET-1 were recovered on the filter. The radioactivity retained on the filter was measured to obtain the amount of ($^{125}$I]ET-1 bound to the ETB receptors. The amount of ($^{125}$I]ET-1 bound in the presence of ET-1 in great excess as the test compound was taken as the amount of nonspecific binding. The amount of specific binding (SPB) of [$^{125}$I]ET-1 was obtained by subtracting the amount of nonspecific binding from the total amount of binding determined. The percent SPB value at test compound concentration C (molar concentration by volume) was defined as the percent ratio of the amount of specific binding relative to the amount of specific binding obtained at a test compound concentration of 0. The thus-obtained value was substituted for the following "pseudo-Hill's equation" to calculate the test compound concentration (IC$_{50}$ value) required to have a value of 50% for the amount of specific binding of [$^{125}$I]ET-1.
log[%SPB/(100 - %SPB)]=n[logC - log(IC$_{50}$)]
   n: Pseudo-Hill's coefficient
(3) Using the peptides of Examples 1 through 3 and Reference Example 1, IC$_{50}$ values for ET$_A$ receptors and ET$_B$ receptors were calculated. The results are given below.

| Peptide | IC$_{50}$ (M) for ET$_A$ | IC$_{50}$ (M) for ET$_B$ |
| --- | --- | --- |
| Example 1 | 1.8 × 10$^{-10}$ | 1.1 × 10$^{-8}$ |
| Example 2 | 1.8 × 10$^{-10}$ | 2.8 × 10$^{-8}$ |
| Example 3 | 4.9 × 10$^{-10}$ | 1.4 × 10$^{-8}$ |
| Reference Example 1 | 0.8 × 10$^{-10}$ | 12.0 × 10$^{-8}$ |

These results demonstrate that the peptides of the present invention excellently antagonize ET$_A$ receptors and ET$_B$ receptors, and that they are more potent in ET$_B$ receptor antagonistic action than in ET$_A$ receptor antagonistic action, in comparison with the peptide disclosed in EP0528312A2.

Test Example 2
Determination of porcine coronary vein relaxation activity

Ring preparations of porcine coronary vein (3 mm in a diameter) were placed in an organ bath filled with Krebs solution gassed with 95% $O_2$/5%$CO_2$ at 37° C. and allowed to stand for 1.5 h at a resting load of 0.5 g tension for vein. The preparations were constricted with 60 mM KCl for 15 min and then washed and allowed to stand for 1.5 h at the resting load. The vein preparations constricted with sarafotoxin S6c (S6c) at 1 nM for 45 min were used to determine the effect of the peptide of Example 4 at 0.01 μM. Result is shown in the following Table as the relaxation rate relative to the constriction of S6c (100%).

| Peptide | relaxation rate (%) |
|---|---|
| Example 4 | 66 |

The result demonstrates that the peptide of the present invention excellently possesses a vascular smooth muscle relaxation activity.

Test Example 3

A preparation as obtained in Formulation Example 1 or Comparative Formuration 1 as a control group was subcutaneously administered to the back of 8-week-old male Wistar fatty rats every four weeks. The male Wistar fatty rat, a line of rat which genetically develops obesity and hyperglycemia, is characterized by increased leakage of protein and albumin in urine with the development of hyperglycemia. A dosage of the preparation as obtained in Formulation Example 1 was 3 mg per one rat (58 mg per one rat as the microcapsules). A dosage of Comparative Preparation 1 was 200 mg per one rat. The results of urinary albumin assays in a control group and an administration group of Formulation Example 1 are given in Table 1.

TABLE 1

| Urinary Albumin (mg/day, mean) | | | |
|---|---|---|---|
| Weeks after administration | 0 | 3 | 6 |
| Control group | 3 | 10 | 27 |
| Formulation Example 1 | 3 | 6 | 9 |

As seen in Table 1, during the period of about 6 weeks after Formulation Example 1 administration, smaller amounts of albumin were excreted in the urine, in comparison with control velues. These results demonstrate that urinary albumin excretion, a symptom of diabetic nephropathy, were suppressed during the perod when the endothelin antagonist was sustained in the live body as shown in Test Example 3, suggesting the utility of the present invention as a therapy for diabetic nephropathy.

What is claimed is:

1. A cyclic hexapeptide having endothelin B receptor antagonistic action represented by the formula:

cyclo-{D—Asp—L—Asp—(B1)—L—Asp—D—γMeLeu—L—Leu—D—Trp—} with Asp(B1) being aspartic acid β-4-phenylpiperazine amide and γMeLeu being gamma methylleucine, or a salt thereof.

2. A cyclic hexapeptide having endothelin B receptor antagonistic action represented by the formula:

cyclo—{D—Asp—L—Asp—(B7)—L—Asp—D—γMeLeu—L—Leu—D—Trp—} with Asp(B7) being aspartic acid β-4-(2-methoxyphenyl) piperazine amide and γMeLeu being gamma methylleucine, or a salt thereof.

3. A cyclic hexapeptide having endothelin B receptor antagonistic action represented by the formula:

cyclo—{D—Asp—L—Asp—(B7)—L—Asp—D—γMeLeu—L—Leu—D—Trp(Ac)—} with Asp(B7) being aspartic acid β-4-(2-methoxyphenyl) piperazine amide, γMeLeu being gamma methylleucine and Trp (Ac) being $N^{in}$-acetyltryptophan, or a salt thereof.

4. An endothelin B receptor antagonist composition which comprises an effective amount of a cyclic hexapeptide represented by the formula cyclo—{—D—Asp—L—Asp(B1)—L—Asp—D—γMeLeu—L—Leu—D—Trp—} with Asp(B1) being aspartic acid β-4-phenylpiperazine amide and γMeLeu being gamma methylleucine, cyclo{—D—Asp—L—Asp(B7)—L—Asp—D—γMeleu—L—Leu—D—Trp—} with Asp(B7) being aspartic acid β-4-(2-methoxyphenyl) piperazine amide and γMeLeu being gamma methylleucine, or cyclo{—D—Asp—L—Asp(B7)—L—Asp—D—γMeLeu—L—Leu—D—Trp(Ac)—} with Asp(B7) being aspartic acid β-4-(2-methoxyphenyl) piperazine amide, γMeLeu being gamma methylleucine and Trp (Ac) being $N^{in}$-acetyltryptophan, or a pharmacologically acceptable salt thereof;

and a pharmaceutically acceptable carrier.

5. A pharmaceutical composition for suppressing vascular smooth muscle contractions caused by endothelin which comprises an effective amount of the cyclic hexapeptide represented by the formula cyclo{—D—Asp—L—Asp(B1)—L—Asp—D—γMeLeu—L—Leu—D—Trp—} with Asp(B1) being aspartic acid β-4-phenylpiperazine amide and γMeLeu being gamma methylleucine, cyclo{—D—Asp—L—Asp(B7)—L—Asp—D—γMeLeu—L—Leu—D—Trp—} with Asp(B7) being aspartic acid β-4-(2-methoxyphenyl) piperazine amide and γMeLeu being gamma methylleucine, or cyclo{—D—Asp—L—Asp(B7)—L—Asp—D—γMeLeu—L—Leu—D—Trp(Ac)—} with Asp(B7) being aspartic acid β-4-(2-methoxyphenyl) piperazine amide, γMeLeu being gamma methylleucine and Trp (Ac) being $N^{in}$-acetyltryptophan, or a pharmacologically acceptable salt thereof;

and a pharmaceutically acceptable carrier.

* * * * *